United States Patent [19]

Gustafson et al.

[11] 4,169,891

[45] Oct. 2, 1979

[54] METHOD FOR THE CONTROL OF SWINE DYSENTERY WITH ANTIBIOTIC BM123γ AND CERTAIN DERIVATIVES THEREOF

[75] Inventors: Richard H. Gustafson, Lawrenceville; Gordon A. Kemp, Princeton, both of N.J.

[73] Assignee: American Cyanamid Company, Stamford, Conn.

[21] Appl. No.: 925,661

[22] Filed: Jul. 17, 1978

[51] Int. Cl.$^2$ .............................................. A61K 31/71
[52] U.S. Cl. .................................................... 424/181
[58] Field of Search ......................................... 424/181

[56] References Cited

U.S. PATENT DOCUMENTS

| | | | |
|---|---|---|---|
| 4,007,167 | 2/1977 | Martin et al. | 424/181 |
| 4,018,972 | 4/1977 | Hlavka | 424/181 |
| 4,048,431 | 9/1977 | Hlavka et al. | 424/181 |

*Primary Examiner*—Sam Rosen
*Attorney, Agent, or Firm*—H. G. Jackson

[57] ABSTRACT

The invention is a novel method for the control of swine dysentery, comprising orally administering to swine pharmaceutically effective amount of antibiotic BM123γ, pharmaceutically acceptable salts, complexes and alkyl derivatives thereof, in, or with the animals feed. The invention further relates to antibiotic BM123γ, pharmaceutically acceptable salts, complexes and alkyl derivatives thereof, useful for the control of swine dysentery.

7 Claims, No Drawings

METHOD FOR THE CONTROL OF SWINE DYSENTERY WITH ANTIBIOTIC BM123γ AND CERTAIN DERIVATIVES THEREOF

Among the enteric diseases which affect swine, one of the most common is swine dysentery. This disease is most prevalent among 8–14 week old pigs, although it also occurs in suckling pigs and adult swine.

Frequently characterized as mucohemorrhagic diarrhea, swine dysentery is a highly contagious disease, and it is not uncommon to have an incidence of over 90% among swine reared in close confinement with a mortality rate of 30 to 70% depending on the effectiveness of treatment.

Infection occurs via the wastes of infected animals to which a herd is exposed and is in close contact with, as in confined quarters, and since for the sake of efficiency and production an ever increasing number of swine are raised by the pork industry in close confinement, obviously a sudden outbreak of swine dysentery may result in significant and costly production losses for the industry.

Consequently, it is of great interest to the pork industry to prevent and/or control the outbreak of swine dysentery in a herd.

We now find, that by the novel method of the invention, swine dysentery can be controlled by orally administering to swine pharmaceutically effective amount of antibiotic BM123γ, pharmaceutically acceptable salts, complexes, and alkyl derivatives thereof, wherein the antibiotic is represented by formula (I) of the following structure:

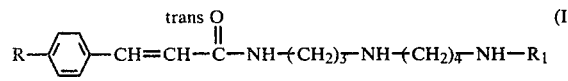

wherein $R_1$ is hydrogen, alkyl $C_1$–$C_{10}$, halo substituted alkyl $C_2$–$C_6$, or hydroxy substituted alkyl $C_2$–$C_6$; and wherein R is a moiety of

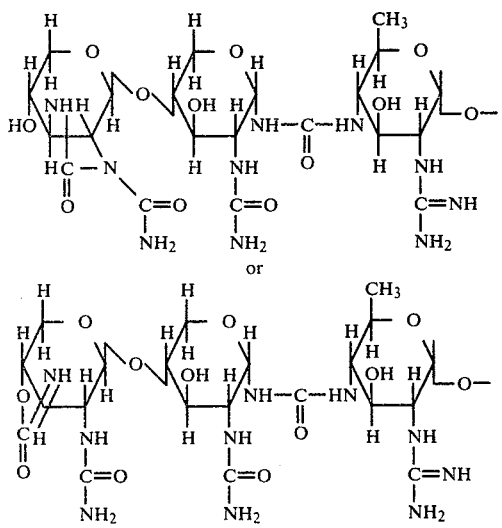

and mixtures thereof.

A preferred group of compounds represented by formula (I) are those, wherein $R_1$ is hydrogen, isopropyl, 1,3-dimethylbutyl, 1,3,3-trimethylbutyl, 1,2-dimethylpentyl, 1-methylnonyl, 1-ethyl-3-chloropropyl or 1-methyl-2-hydroxypropyl.

In accordance with this invention, swine dysentery may be effectively controlled by administering antibiotic BM123γ, pharmaceutically acceptable salts, complexes or alkylated derivatives thereof to the host animal in, or with the feed in an amount equivalent to between 0.0001% to 0.01% (1 to 100 ppm) and preferably 0.0005% to 0.002% (5 to 20 ppm) by weight of feed daily.

In practice, the active material will generally be formulated as a premix and/or animal feed supplement which is admixed with a nutritionally balanced feed or added to the feed as a top dressing, or the like.

Premixes may be prepared by blending about 70% to 99% by weight of rice flour, ground rice hulls, ground corn, or the like, with about 1% to 30% by weight of antibiotic BM123γ, pharmaceutically acceptable salts, complexes or alkylated derivatives thereof.

Antibiotics BM123γ$_1$ and γ$_2$ (hereinafter referred-to as antibiotic BM123γ) are formed by fermentative biosynthesis during the cultivation under controlled conditions of a new strain of an undetermined species of Nocardia, NRRL 5646, and, in particular, by a mutant strain of NRRL 5646, namely NRRL 8050 and more particularly by an X-ray mutant of NRRL 8050, namely Lederle KL 1192, a viable culture of which has been deposited with the Culture Collection Laboratory, Northern Utilization Research and Development Division, U.S. Department of Agriculture, Peoria, Illinois and has been added to its permanent collection under their accession number NRRL 11230 where it is freely available to the public.

The preparation and properties of these antibiotics are set forth in U.S. Pat. No. 4,007,167 (1977), U.S. Pat. No. 4,018,972 and U.S. Pat. No. 4,048,431.

Lederle KL 1192 (NRRL 11230) has cultural, physiological and morphological characteristics essentially the same as those of NRRL 8050.

The problem of recovering antibiotics BM123γ$_1$, and γ$_2$ economically is a serious one. Column chromatography, absorption on charcoal and elution with copious amounts of organic solvents are usually employed. Such processes are excessively expensive for recovering an antibiotic for veterinary use for oral administration to animals incorporated or added to their feed.

In an effort to overcome this problem, several processes have been developed whereby precipitation of the antibiotic from the whole or filtered fermentation broth is accomplished by the addition of an alkali metal sulfate of structure $CH_3(CH_2)_nOSO_3M$ wherein M is sodium or potassium and n is an integer of 9 to 17, typical such alkali metal alkyl sulfates are, for example, sodium decyl sulfate, potassium hendecyl sulfate, sodium lauryl sulfate, sodium cetyl sulfate, sodium octadecyl sulfate, and the like. The antibiotics may also be precipitated from the fermentation broth with sodium dioctyl sulfosuccinate or a "syntan" compound.

Syntan compounds are synthetic tanning agents of sulfated phenol formaldehyde type, which may be represented by the following general formula:

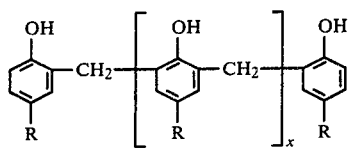

wherein R is hydrogen or methylene sulfonic acid (—$CH_2$—$SO_3$); X is 0, 1, 2, 3 or 4 with the proviso that about half of the R groups are methylene sulfonic acid groups. This synthetic tanning agent is not a pure chemical compound but of necessity is obtained as a mixture having an estimated molecular weight of 420–530. It is readily prepared by first condensing phenol and formaldehyde in aqueous media followed by reaction of the intermediate condensate with formaldehyde, various sulfites and buffer acids thus forming ω-sulfonic acid groups in the molecules. The product is an amorphous water soluble material that may be obtained as an aqueous concentrate or in powder form, and ranges from colorless to dark brown. In order to avoid cumbersome language, this synthetic tanning agent is referred-to by its generic name in the art as "syntan" and this term is used in the specification and appended claims. A syntan of the above general formula is sold by A. J. and J. O. Pillar. Inc. of Newark, N.J. under the trade name of Tru-Tan ® RT New.

The above complexes have been referred to as reversible antibiotic-alkyl sulfate, -dioctyl sodium sulfosuccinate, and -syntan complexes. Their exact chemical nature has not been determined but covalent bonding is not involved, and the products are not physical mixtures. Nor are they necessarily combined in any limiting stoichiometry. The chemical bonds are reversible since the antibacterials may be recovered from the complexes by various means.

It seems possible, that the above complexes are sufficiently reversible so that under conditions of use as feed additives, the antibiotic is set free in the host animals digestive system.

Pharmaceutically acceptable acids, which may be used to prepare salts of the above antibiotics are, among others, hydrochloric acid, sulfuric acid, phosphoric acid, citric acid and tartaric acid, and the like.

Should it be desired, the antibiotic BM123γ, salts, complexes and alkylated derivatives thereof may also be administered to the swine in their drinking water.

Alternatively, pills, tablets, boluses, and the like, containing the above active compound and suitable for oral administration, may be prepared by known and pharmaceutically acceptable methods.

We, however, prefer oral administration of the antibiotic for the control of swine dysentery, to the host animals in, or with their feed.

The following examples serve to further illustrate the novel method of the invention.

EXAMPLE I

In vivo Evaluation of the Efficacy of Antibiotic BM123γ for the Control of Swine Dysentery Test Drug Antibiotic BM123γ hydrochloride, administered to the animals in their feed at the rate indicated in Table I below.

Test Animals

Castrated male, and female pigs, 5–6 weeks of age and weighing 8–9 kg are randomly allotted to pens of eight (4 males and 4 females). A pen of each is used for noninfected and infected controls, and two pens are allotted at each level of drug tested. Infected groups acquired the disease naturally by association with infectious material in their pens and environment. The disease was confirmed as swine dysentery by unmistakable clinical signs and by demonstration of *Treponema hyodysenteriae* in clinical material.

Procedure

The animals are offered a swine grower ration (table of composition attached hereinbelow) and water ad libitum. All groups receive the same feed, excepting that the treated animals receive the test drug incorporated in their feed at the levels indicated in Table I below. The animals are observed daily for symptoms of swine dysentery and mortality counts are made. Weight gains are determined at four and at six weeks. The results obtained are summarized in Table I below.

| Swine Grower Ration | |
|---|---|
| Ingredient | lbs |
| Ground yellow corn | 1560 |
| Soybean oil meal (49% protein) | 400 |
| Dicalcium Phosphate (18.5% P) | 15 |
| Iodized Salt | 10 |
| Limestone (38% Ca) | 12 |
| Mineral Premix* | 1.5 |
| Vitamin Premix** | 1.5 |
| | 2000.0 |

| *Mineral Premix | |
|---|---|
| Ingredient | % |
| Iron | 10 |
| Zinc | 10 |
| Manganese | 6 |
| Copper | 1 |
| Corn, q.s. ad | 100 |

| **Vitamin Premix | |
|---|---|
| Ingredient | Per Pound |
| Vitamin A | 2,000,000 I.U. |
| Vitamin $D_3$ | 400,000 I.U. |
| Vitamin E | 5,000 I.U. |
| Vitamin $B_{12}$ | 10 mg |
| Riboflavin | 4,000 mg |
| Niacin | 20,000 mg |
| d-Pantothenic acid (Ca-pantothenate) | 10,000 mg |
| Menadione (Menadione-sodium bisulfite complex) | 1,049 mg |
| Composition | |
| Ground rice hulls, Vitamin A acetate in gelatin - sugar - starch beadlet, Vitamin A acetate with D-activated animal sterol (source of Vitamin $D_3$) in gelatin - sugar - starch beadlet, dl - alpha - tocopheryl acetate, vitamin $B_{12}$ supplement, Riboflavin supplement, Niacin supplement, Calcium Pantothenate, Menadione Sodium Bisulfite Complex. | |

TABLE I

Evaluation of the Efficacy of Antibiotic BM123γ-hydrochloride for the control of Swine dysentery in pigs.

|  |  | Level of drug in Feed | No. of | 4 - Weeks data | | | | 6- weeks data | | | |
|---|---|---|---|---|---|---|---|---|---|---|---|
|  |  |  |  | Average wt/ pig in kg. | | No. of Pigs with | | Average wt/ pig in kg. | | No. of Pigs with | |
| No. | Experiment | (ppm) | Pigs | Initial | Final | diarrhea | dead | Initial | Final | diarrhea | dead |
| 1 | Control non-infected | — | 8 | 9.1 | 14.8 | 0 | 0 | 9.1 | 21.1 | 0 | 0 |
| 2 | Control infected | — | 8 | 8.4 | 17.1 | 3 | 1 | 8.4 | 24.1 | 4 | 4 |
| 3 | antibiotic | 5 | 16 | 8.6 | 16.1 | 4 | 1 | 8.6 | 19.9 | 6 | 2 |
| 4 | BM123γ | 10 | 16 | 8.7 | 17.7 | 4 | 1 | 8.7 | 20.8 | 9 | 5 |
| 5 | hydrochloride | 20 | 16 | 8.7 | 20.8 | 0 | 0 | 8.7 | 27.8 | 0 | 1* |

*Pig died from causes other than swine dysentery.

EXAMPLE 2

In vitro Activity of Antibiotic BM123γ, Various Salts and Alkyl Derivatives Thereof against *Treponema hyodysenteriae*

The compounds are dissolved in 1 ml DMSO (unless otherwise indicated in Table II below) are ten fold serial dilutions are made in DMSO to yield from 100 to 0.001 mcg/disc when 0.02 ml of each dilution is placed on a sterile filter paper disc.

Cultures of *T. hyodysenteriae*, grown overnight in trypticase-soy broth are spread on trypticase-soy-agar + 5% sheep blood plates and appropriate discs placed on the surface. The plates are incubated at 37° C. for three days and then read.

Growth of *T. hyodysenteriae* is evidenced by hemolysis. Zones of no hemolysis surrounding a disc indicate inhibition and are measured in mm. Uniformity of growth is taken into consideration in the determination of zone sizes. The lowest concentration which prevents hemolysis is taken as end point.

The results obtained, are summarized in Table II below.

fold serial dilutions are made in sterile distilled water to yield from 100 to 0.001 mcg/disc when 0.02 mg of each dilution is placed on a sterile filter paper disc. Duplicate discs are heated in an oven at 60° C. for 3 hours.

Growth of *T. hyodysenteriae* is evidenced by hemolysis. Zones of no hemolysis surrounding a disc indicate inhibition and are measured in mm. Uniformity of growth is taken into consideration in the determination of zone sizes. The lowest concentration which prevents hemolysis is taken as end point. N-(5-nitro-2-thiazolyl)acetamide(acinitrazole) is used as standard. The results are summarized in Table III below.

TABLE III

In vitro efficacy of BM123γ HCl for inhibiting the growth of *Treponema hyodysenteriae*, using acinitrazole as standard.

| Isolate No. | Lowest inhibiting concentrations (mcg/ml) of | | | |
|---|---|---|---|---|
|  | BM123γ | HCl | Acinitrazole | |
|  | Unheated disc | heated disc | unheated disc | heated disc |
| 1 | 10 | 10 | 0.1 | 0.01 |
| 2 | 10 | 10 | 0.1 | 0.1 |
| 3 | 10 | 100 | 0.1 | 0.01 |

TABLE II

In vitro activity of Antibiotic BM123γ, various salts and alkyl derivatives thereof against *Treponema hyodysenteriae*.

| Antibiotic BM123γ-salts and alkyl derivatives | Percent real | Lowest disc concentration in meg inhibiting growth of *T. hyodiseuteriae* | Remarks |
|---|---|---|---|
| hydrochloride | 60 | 1.0 |  |
| hydrochloride, spray dried filtrate | 0.933 | — | at higher dilution hemolyzed blood, no inhibition readings were possible |
| sodium lauryl sulfate salt | 0.447 | — | " |
| Feed grade sodium lauryl sulfate salt | 47.0 | 10.0 | at higher dilutions hemolyzed blood |
| dioctyl sulfosuccinate salt | 38.6 | 10.0 | " |
| isopropyl | 100.0 | 1.0 |  |
| 1-methylnonyl | 100.0 | 10.0 |  |
| 1,3-dimethylbutyl | 98.0 | 1.0 |  |
| 1,3,3-trimethylbutyl | 100.0 | 10.0 |  |
| 1,2-dimethylpentyl | 30.0 | 10.0 | at higher dilutions hemolyzed blood |

EXAMPLE 3

In vitro Activity of BM123γ HCl against Three Strains of *Treponema hyodysenteriae*

Strains of *Treponema hyodysenteriae* originally isolated from clinical cases of swine dysentery are grown on a trypticase-soy-agar (TSA)+5% sheep blood medium for three days at 37° C. under anaerobic conditions. Previously reduced TSA+5% sheep blood plates are then streaked with 0.1 ml agar plugs taken from the edge of hemolytic areas on the inoculum plates.

One ml of sterile, distilled water is added to 5 mg of drug and the mixture agitated until homogeneous. Ten-

EXAMPLE 4

Preparation of Antibiotic BM123$\gamma$1 and $\gamma$2-Lauryl Sulfate Complex from Whole Harvest Mash A 28 liter portion of Nocardia NRRL 11230 (Lederle KL1192) fermentation mash containing 571 mcg. of antibiotic BM123$\gamma$1 and $\gamma$2 per ml. is adjusted to pH 2.0 with dilute sulfuric acid. A 218 g. portion of sodium lauryl sulfate is added and the pH is readjusted to 2.0 with dilute sulfuric acid. The mixture is stirred for 45 minutes, 60 g. of diatomaceous earth is added and the mixture is filtered. The solid complex is dried in vacuo at 40° C. for 67 hours giving 1.4 kg of material containing BM123γ1 and γ2 complex.

EXAMPLE 5
Preparation of Antibiotic BM123γ1 and γ2-Lauryl Sulfate Complex from Harvest Mash Filtrate To 6 liters of Nocardia NRRL 11230 (Lederle KL1192 fermentation mash filtrate containing 447 mcg. of antibiotic BM123γ1 and γ2 per ml there is added with stirring 90.0 g of diatomaceous earth followed by 420 ml of 10% w/v aqueous sodium lauryl sulfate. The pH of the suspension is adjusted to 2.5 with 50% w/w sulfuric acid, stirred for 15 minutes and then filtered. The filter cake is rinsed with a small amount of water and then dried for three days in vacuo without heat, giving 223.4 of product assaying 4.9 mcg/mg.

EXAMPLE 6
Preparation of Antibiotic BM123γ1 and γ2-Dioctyl Sulfosuccinate Complex from Harvest Mash Filtrate To a 40 liter portion of Nocardia NRRL 11230 (Lederle KL1192) fermentation mash filtrate containing 533 mcg of antibiotic BM123γ1 and γ2 per ml, is added 800 g of sodium chloride. The filtrate is adjusted to pH 4 with hydrochloric acid. A 600 g portion of diatomacious earth is added followed by one liter of an aqueous alcoholic solution of dioctyl sodium sulfosuccinate. The pH is readjusted to 4.0 with hydrochloric acid, 600 g. of diatomaceous earth is added and the mixture is stirred for 15 minutes. The mixture is allowed to settle for one hour and the supernatant is syphoned off. The pH of the settled material is adjusted to 5 with sodium hydroxide. The mixture is then freeze dried giving 3.02 kg of material containing antibiotic BM123γ1 and γ2-dioctyl sulfosuccinate complex.

EXAMPLE 7
Preparation of Antibiotic BM123γ1 and γ2-Dioctyl Sodium Sulfosuccinate Complex from Harvest Mash Filtrate To a 100 ml portion of Nocardia NRRL 11230 (Lederle KL1192) mash filtrate, assaying 582 mcg/ml of antibiotic BM123γ1 and γ2, is added with stirring 1.0 ml of a 70% ethanolic solution of dioctyl sodium sulfosuccinate. The pH of the mixture is adjusted to 4.75 with 6 N hydrochloric acid and the precipitate is dried in vacuo for 4 days without heat to give 1.5 g of product.

EXAMPLE 8
Preparation of Antibiotic BM123γ1 and γ2-Syntan Complex from Whole Harvest Mash Thirty liters of Nocardia NRRL 11230 (Lederle KL1192) fermentation mash containing 347 mcg of BM123γ1 and γ2 antibiotic per ml is used at harvest pH 5.7. A 750 ml portion of Trutan ® RT New [a synthetic tanning agent (A. J. and J. O. Pilar, Inc.)] is added slowly to the mash with stirring. The mixture is stirred for one hour, 600 g of diatomaceous earth is added and the mixture is filtered. The filter cake is dried in vacuo at 40° C. for 48 hours, giving 1.5 kg of dried material containing antibiotic BM123γ1 and γ2 complex.

EXAMPLE 9
Preparation of Antibiotic BM123γ1 and γ2-Syntan Complex from Harvest Mash Filtrate To 3 liters of stirred Nocardia NRRL 11230 (Lederle KL1192) fermentation mash filtrate, assaying 475 mcg of antibiotic BM123γ1 and γ2 per ml is added 52.5 ml of Trutan ® RT New. The pH of the resultant slurry is adjusted to 4.75 with 6 N hydrochloric acid, stirred for 5 minutes and allowed to settle for 45 minutes. The solids are recovered by filtration, washed with a small amount of water and dried in vacuo, without heat, giving 35.8 g of product.

We claim:

1. A method for the control of swine dysentery comprising orally administering to swine a pharmaceutically effective amount of an antibiotic of formula

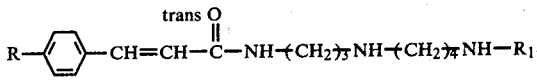

wherein $R_1$ is hydrogen, alkyl $C_1$-$C_{10}$, alkyl $C_2$-$C_6$ mono-substituted with halogen or hydroxy; R is a moiety of

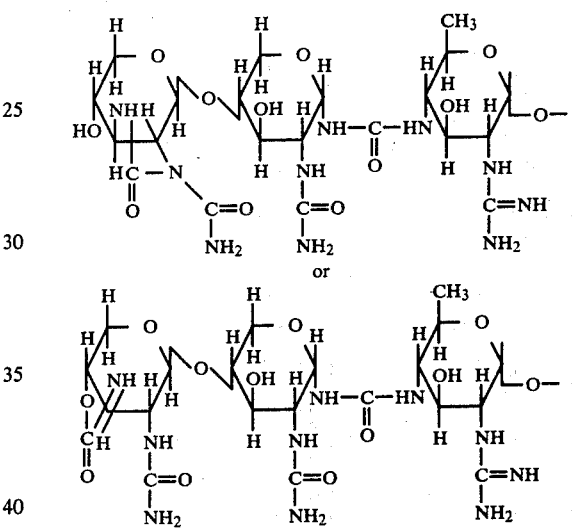

or mixtures thereof; pharmaceutically acceptable salts, or complexes thereof, in the animal feed.

2. A method according to claim 1, wherein $R_1$ is hydrogen, isopropyl, 1,3-dimethylbutyl, 1,3,3-trimethylbutyl, 1,2-dimethylpentyl, 1-methylnonyl, 1-ethyl-3-chloropropyl or 1-methyl-2-hydroxypropyl.

3. A method according to claim 1, wherein $R_1$ is hydrogen or isopropyl.

4. A method according to claim 1, wherein the salts are hydrochloride, sulfate, phosphate, citrate, or tartrate; the complexes are an alkyl sulfate of formula $CH_3(CH_2)_n$—$OSO_3M$ wherein n is an integer of 9 to 7, M is sodium or potassium, dioctylsulfosuccinate or a syntan.

5. A method according to claim 4, wherein the salt is the hydrochloride, and complexes are dilauryl sulfate, dioctyl sulfosuccinate or syntan complex of the antibiotic.

6. A method according to claim 1, wherein the antibiotic is administered to swine daily in amounts from 1 ppm to 100 ppm by weight of feed.

7. A method according to claim 6, wherein $R_1$ is hydrogen, the antibiotic is the hydrochloride, and is administered to swine daily in amounts from 5 ppm to 20 ppm by weight of feed.

* * * * *